United States Patent
Ancona et al.

(10) Patent No.: US 11,067,508 B2
(45) Date of Patent: *Jul. 20, 2021

(54) ENZYME TRANSDUCERS AND SENSORS BASED ON DNA LOOPS

(71) Applicant: The Government of the United States of America, as represented by the Secretary of the Navy, Arlington, VA (US)

(72) Inventors: Mario Ancona, Alexandria, VA (US); Hieu Bui, Alexandria, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,286

(22) Filed: Apr. 14, 2020

(65) Prior Publication Data
US 2020/0326283 A1  Oct. 15, 2020

Related U.S. Application Data

(60) Provisional application No. 62/833,953, filed on Apr. 15, 2019.

(51) Int. Cl.
| | |
|---|---|
| *G01N 21/64* | (2006.01) |
| *G01N 33/52* | (2006.01) |
| *G01N 33/542* | (2006.01) |
| *C12Q 1/00* | (2006.01) |

(52) U.S. Cl.
CPC .......... *G01N 21/6428* (2013.01); *C12Q 1/005* (2013.01); *G01N 33/52* (2013.01); *G01N 33/542* (2013.01); *G01N 2021/6432* (2013.01)

(58) Field of Classification Search
CPC ....................................................... C12Q 1/37
See application file for complete search history.

(56) References Cited

PUBLICATIONS

Wang et al., Angew Chem Int Ed Engl., 2009, 48(5):856-870 or pp. 1-34 as printed.*
Seeman NC. Structural DNA nanotechnology: an overview. Methods Mol Biol. 2005;303:143-166. doi:10.1385/1-59259-901-X:143.
Tyagi S, Kramer FR. Molecular beacons: probes that fluoresce upon hybridization. Nat Biotechnol. 1996;14 (3):303-308. doi:10.1038/nbt0396-303.
Yurke B, Turberfield AJ, Mills AP Jr, Simmel FC, Neumann JL. A DNA-fuelled molecular machine made of DNA. Nature. 2000;406(6796):605-608. doi:10.1038/35020524.
Seelig G, Soloveichik D, Zhang DY, Winfree E. Enzyme-free nucleic acid logic circuits. Science. 2006;314 (5805):1585-1588. doi:10.1126/science.1132493.
Wu C, Cansiz S, Zhang L, et al. A Nonenzymatic Hairpin DNA Cascade Reaction Provides High Signal Gain of mRNA Imaging inside Live Cells. J Am Chem Soc. 2015;137(15):4900-4903. doi:10.1021/jacs.5b00542.

* cited by examiner

*Primary Examiner* — Bin Shen
(74) *Attorney, Agent, or Firm* — US Naval Research Laboratory; Roy Roberts

(57) ABSTRACT

The stiffness and topology of ultra-small circular DNAs and DNA/peptide hybrids are exploited to create a transducer of enzyme activity with low error rates. The modularity and flexibility of the concept are illustrated by demonstrating various transducers that respond to either specific restriction endonucleases or to specific proteases. In all cases the output is a DNA oligo signal that, as we show, can readily be converted directly to an optical readout, or can serve as input for further processing, for example, using DNA logic or amplification By exploiting the DNA hairpin (or stem-loop) structure and the phenomenon of strand displacement, an enzyme signal is converted into a DNA signal, in the manner of a transducer. This is valuable because a DNA signal can be readily amplified, combined, and processed as information.

3 Claims, 7 Drawing Sheets

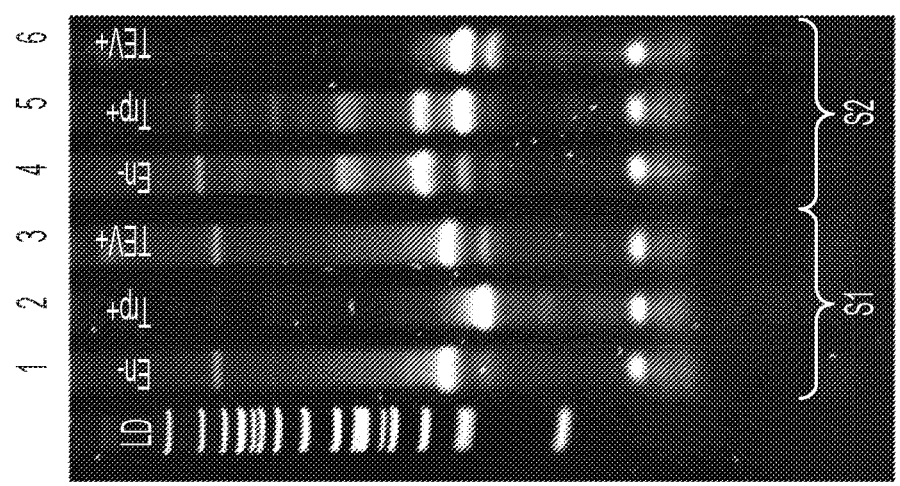
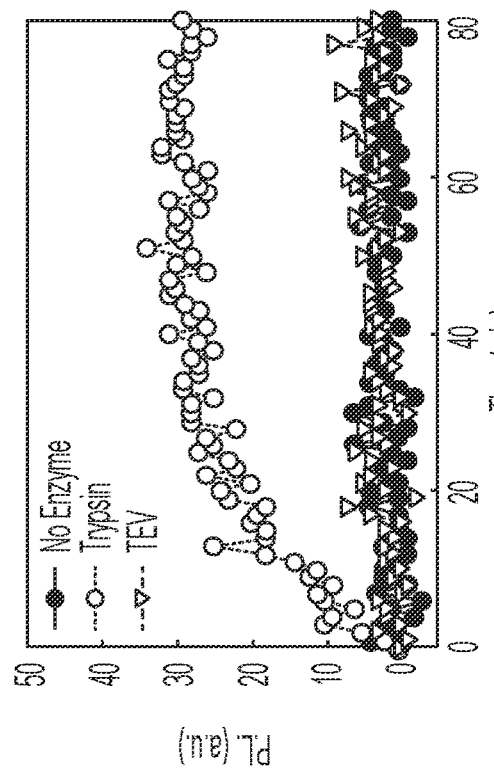
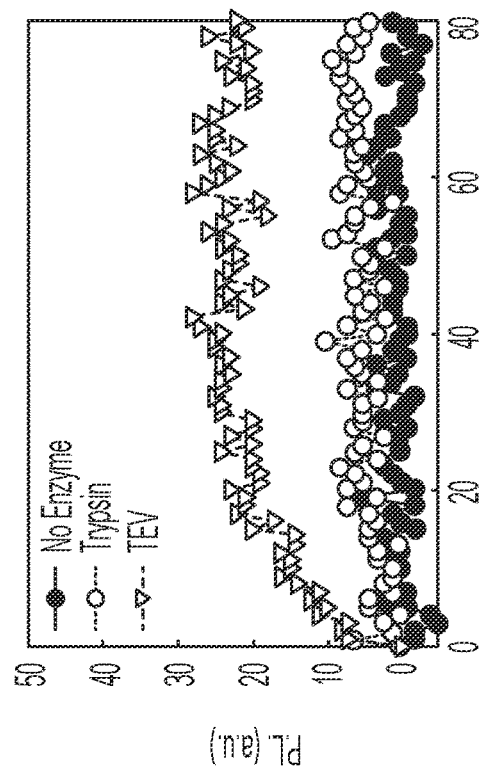
FIG. 4A
FIG. 4B
FIG. 4C

ENZYME TRANSDUCERS AND SENSORS BASED ON DNA LOOPS

CROSS-REFERENCE TO RELATED APPLICATIONS

This Application claims the benefit of U.S. Provisional Patent Application No. 62/833,953 filed Apr. 4, 2019, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 110,926.

BACKGROUND

Enzymes are protein catalysts vital to nearly all biology, allowing nature to perform the myriad room-temperature or near-room-temperature biochemical syntheses that make life possible. A measure of the importance of these processes is that enzymes constitute one quarter of the translation products of the human genome (roughly 500 genes). Furthermore, enzymes are not only key elements of healthy cell activities, but they are also crucial for disease processes and can thus serve as markers for these disease states. As a result, the ability to detect and monitor enzymes such as proteases, esterases, kinases, etc. is a crucial task in a multitude of applications in biology and medicine.

A wide range of enzyme detection systems exist for use in applications in biomedicine, food, etc. Such methods, almost entirely in vitro, can be grouped by the nature of their readouts and the two main classes have optical and electrical outputs. Performance and cost are the two main criteria, and new approaches that have the potential to impact/improve in either of these areas are always welcome. In addition, ideas that have the potential to function in vivo, and can add significant sophistication are of much interest for their potential to broaden capabilities.

A need exists for new techniques for detecting enzyme activity.

BRIEF SUMMARY

Described herein is a technique for enzyme detection/transduction involving conversion to a DNA signal that can in turn be combined, processed, and/or amplified using known DNA methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee FIG. 1 schematically illustrates the concept of the nucleic acid loop sensor/transducer.

FIG. 3B shows photoluminescence data demonstrating confirming the expected behavior of the HaeIII loop sensor while

FIGS. 4A-4C show operation of protease sensors.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

While DNA is of course the basis of genetics, it has also given rise to the field of DNA nanotechnology [1] wherein the information content of the DNA (i.e., its base sequence) is used to program form and/or function for a variety of potential non-biological applications. As described herein, an enzyme signal is converted into a DNA signal, in the manner of a transducer. This is valuable because a DNA signal can be readily amplified, combined, and processed as information. In doing so, two important concepts of relevance are the DNA hairpin (or stem-loop) and strand displacement. Both arise commonly in nature, and both are widely exploited in DNA nanotechnology, e.g., as molecular beacons [2] and for toehold-mediated strand displacement [3]. These capabilities are also utilized jointly for purposes of DNA logic [4] and DNA amplification [5]. The invention disclosed here makes use of all of these ideas.

The subject invention is of this type in that the DNA is employed as both a constructional and a computational material. From a structural standpoint, the transducer is composed largely of DNA. In this it takes particular advantage of two key characteristics of DNA. One is its stiffness that arises from the base-stacking of double-stranded (ds) DNA and that causes DNA to remain straight when shorter than about 15 nm (coherence length). The other relevant property of DNA is its helical nature which can impose topological constraints on the ability of two strands of DNA to hybridize.

Figure 1:
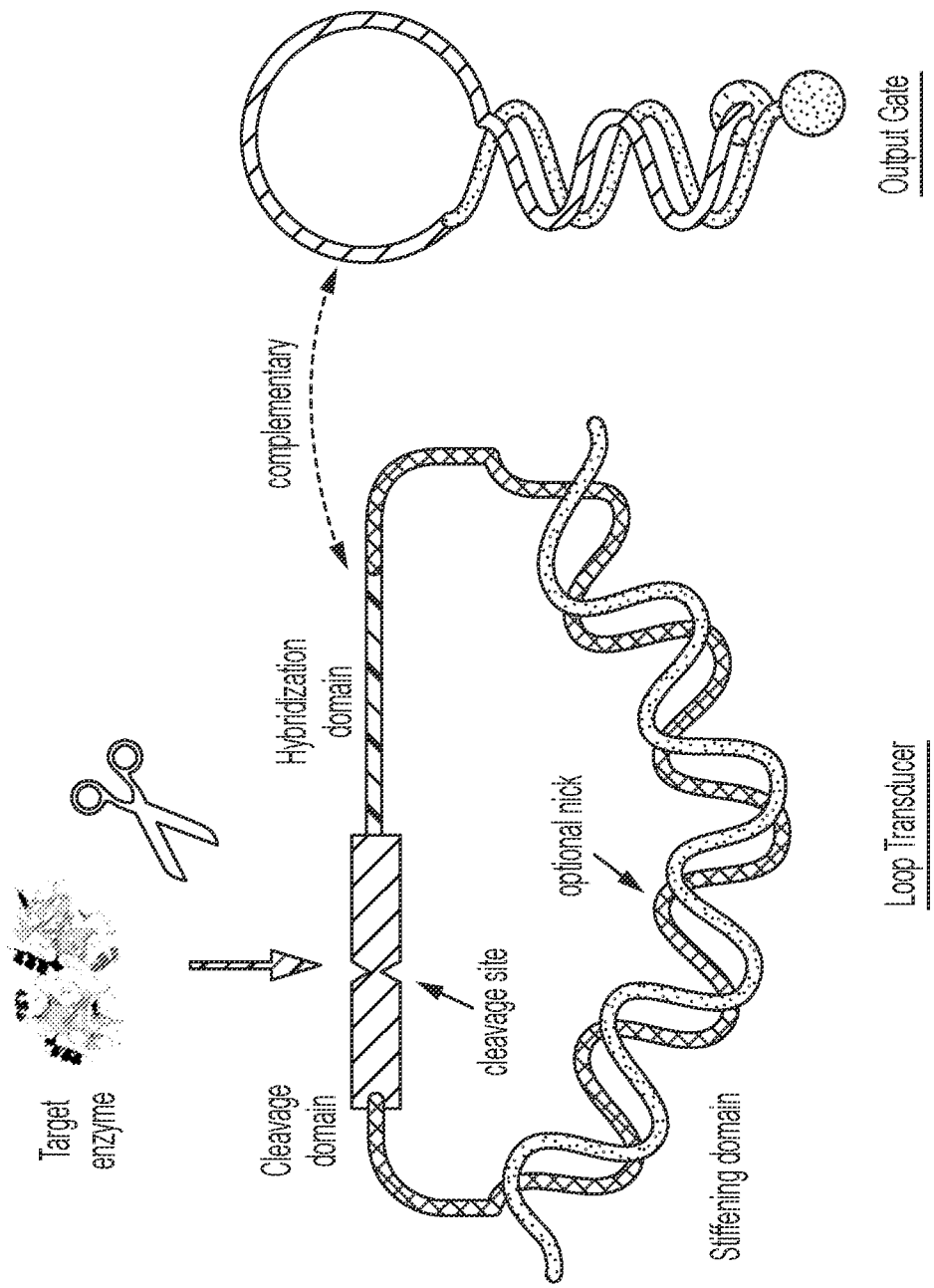

A schematic of the loop sensor concept is shown in FIG. 1. As seen, the basic design of the enzyme-to-DNA transducer consists of the circular DNA or DNA/peptide structure plus an output gate that in simplest form is a conventional molecular beacon. The circular assembly is termed here a 'loop transducer' and, as seen in the figure, comprises three distinct functional domains. The first is a stiffening domain wherein the blue loop strand has a complementary DNA strand (in red) hybridized to it to form a duplex on one side of the loop. Being double-stranded, this section is stiffened by the well-known stacking interactions, and because its length is typically at least half of the total, it keeps the entire loop open with the remaining portions stretched in a 'bow' configuration as shown in FIG. 1. The second domain of the loop transducer is the cleavage domain (in green) that contains the target of the enzyme. The cleavage domain can be single- or double-stranded DNA, RNA, a peptide, or combinations thereof. The third domain is the hybridizing domain which is mostly or all single-stranded DNA that is complementary to DNA in the output gate (on the right in FIG. 1). While the cleavage domain remains intact, the hybridization domain is prevented from hybridizing to the output gate by (i) the aforementioned stress in the loop and (ii) the topological constraint inherent in intertwining two small loops. As a result, if and when the enzyme cleaves the loop, it springs open, relieving both the loop stress and the topological constraint, and thus makes the DNA of the hybridizing domain available to infiltrate and open the hairpin in the output gate by strand displacement. As a result, the fluorophore and quencher pair at the ends of the output gate (depicted in yellow and red) become separated, and the fluorophore now provides a fluorescent signal.

The released hybridizing domain constitutes the DNA output of the loop transducer, and the conversion of this output to a fluorescent signal by the molecular beacon represents the action of this embodiment of the output gate (more complicated output gates are described below). Within the concept just described there are many aspects that can be varied and these may be regarded as of two types, those made with functionality in mind and those associated with optimization. While functionality is obviously of most interest, achieving functionality requires optimization: for example, if the hybridization strand is too short, then the hairpin will never or almost never be open, and vice versa too long a hybridization sequence will tend to leave the hairpin always or almost always open.

Figure 2:
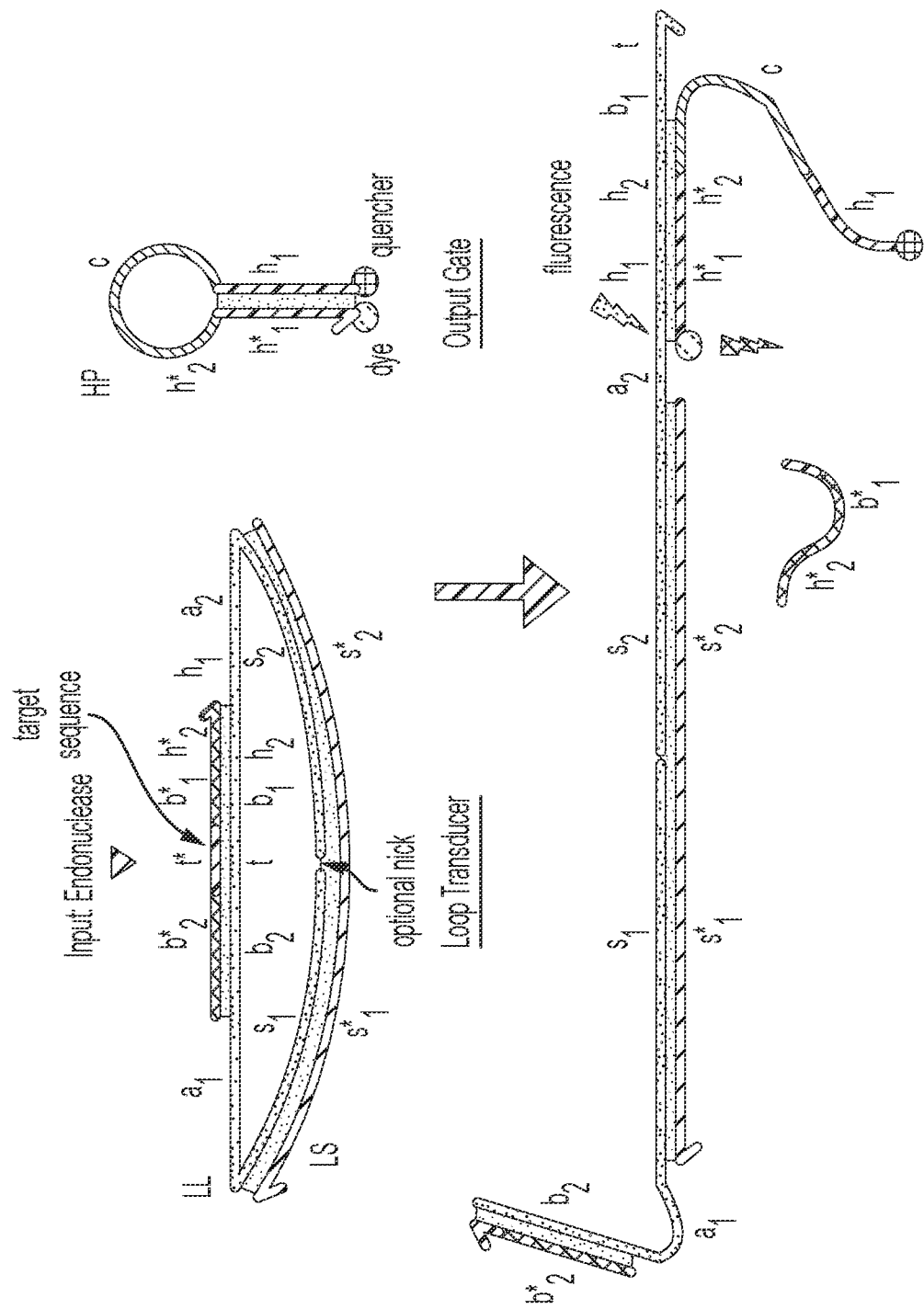
FIG. 2 shows a loop sensor design for endonuclease.

A loop sensor design suitable for detecting endonucleases is shown in FIG. 2. An endonuclease is a type of esterase that cleaves (hydrolyzes) a phosphodiester bond in double stranded DNA (dsDNA) at a specific location determined by the base sequence (with the target and degree of specificity dependent on the particular endonuclease). In this case, the entire structure is formed of DNA. The longest strand (denoted LL) is typically 80 nucleotides long but the length can be varied as desired (for example to within the range of 60 to 100 or even more nucleotides). The loop is closed with the addition of the green stiffening strand (abbreviated as LS). This leaves a nick in the loop that, as verified by molecular dynamics simulation and by experiment, does not compromise the stiffness of the loop transducer so long as the sequence is chosen so that the stacking interaction at the nick is sufficient to maintain the rigidity of the duplex [6]. Nevertheless, from the perspective of susceptibility to melting or degradation (e.g., by enzymatic attack if used in serum or in vivo), one may desire not to have the nick, and it can be eliminated using a T4 ligase. The molecular dynamics simulations were also used as check that the stiffened designs were within the elastic limit of the dsDNA and that buckling was unlikely to occur.

The cleavage domain can be varied to detect different substrates. In the case of an endonuclease sensor, the target sequence should be double-stranded, and this is done by the addition of the LC strand seen in FIG. 2. For protease sensors, this cleavage domain is the peptide substrate of the enzyme(s) of interest. Other possible targets that could be incorporated in the cleavage domain include mRNA or an RNA aptamer.

EXAMPLES

Nuclease Sensing

A loop sensor design suitable for detecting endonucleases was made as shown in FIG. 2, with $\{LL\}=80$, $\{LS\}=47$, $\{LC\}=10$, $\{h\_1\}=8$ and $\{h\_2\}=8$, and $\{c\}=15$, where the bracket notation denotes strand length in nucleotides The loop is closed with the addition of the green stiffening strand (abbreviated as LS). This leaves a nick in the loop that, as verified by molecular dynamics simulation and by experiment, does not compromise the stiffness of the loop transducer so long as the sequence is chosen so that the stacking interaction at the nick is sufficient to maintain the rigidity of the duplex. If desired, the nick can be eliminated using a ligase such as T4 ligase.

Experiments were conducted to evaluate the optimal lengths of sequences forming the transducer and output gate.

The first aspect of the design to be considered for optimization was the hybridizing domain, in particular varying $\{h_1\}$ in the range from 8 to 15 and $\{h_2\}$ in the range from 12 to 27. For the experiments the target sequence in the cleavage domain was that appropriate for HaeIII (GGCC) with the loop design kept fixed with $\{LL\}=80$, $\{LS\}=40$, and $\{LC\}=20$ and only the output gate varied (and simply shifting where the fixed sequences $a_2+h_1$ and $b_1+h_2$ divide as $\{h_1\}$ and $\{h_2\}$ change). Using gel electrophoresis, the various designs were assessed in the presence or absence of the target enzyme. Remarkably, all of the hybridizing domain designs worked well, in all cases showing low levels of both false positives (in the absence of enzyme) and false negatives (in the presence of enzyme). This means that there is considerable flexibility in the design of the output gate and of the hybridizing domain. Moreover, it demonstrates the robustness of the overall design, and the effectiveness of the loop stresses and topology in suppressing unwanted responses.

The second parameter considered for optimization was the length of the stiffening LS strand; tested were lengths of 30, 40, 47, and 55. Fluorescence measurements were made to find the true (false) positive rate from an estimate of the number of hairpins open (closed) when the enzyme is present (absent). The best performing designs have the highest true positive rate (TPR or sensitivity) and the lowest false positive rate (FPR or one minus the specificity). All of the tested stiffening strands give good performance with the LS30 and LS47 designs being best, with the former excelling in specificity and in maintaining a low FPR over long periods of time, while the latter is preferred for sensitivity and for the fastest response within the resolution of the experiment, which was carried out for periods ranging from 2 to 21 hours. The general behavior is a rapid rise to a peak followed by a slow degradation in performance, with again LS47 being best at early times but LS30 performing better over longer times because of its relative immunity to false positives. Finally, control experiments were carried out in which the LS stand was either missing entirely (with a ligated loop) or where it was such that the dsDNA at the nick (in an unligated loop) could bend easily. In both cases strong false positives were observed, with the hairpin being opened by the hybridizing domain even when no endonuclease was present. This shows that the stiffness of the loop is essential to the proper functioning of the transducer.

For loop transducers that respond to endonucleases, another variable to be considered for optimization is the length of the LC strand that comprises the cleavage domain. The specific designs examined had {LC} of 10, 20, and 40, with the hairpin labeled with a donor (Cy3) and an acceptor (Cy5) dye. It was found that the system functioned quite well with {LC}=20, but shows high false positive rates when {LC}=10 and high false negative rates when {LC}=40.

Based on the foregoing, an "optimal" design with {LL}=80, {LS}=30, {LC}=20, $\{h_1\}$=8, $\{h_2\}$=8, and {□}=15 was investigated. Tests were made not just with the endonuclease of interest but also with a different endonuclease (NcoI-HF, targeting CCATGG instead of HaeIII's target GGCC, designed into the transducer) to look for unwanted non-specific signals. FIG. 3A presents results of polyacrylamide gel electrophoresis analysis. Size standards appear in lanes 1 and 8. It was found that in the absence of the target enzyme (HaeIII) and the output gate, the loop transducer remained intact (lane 2), while in the presence of the target enzyme it cleaved, and the associated increase in electrophoretic mobility was observed in lane 3. The analogous experiment with a non-target enzyme NcoI-HF showed no similar transformation as observed in lane 4 (which was essentially unchanged from the no-enzyme case of lane 2). Next introducing the output gate, there was no change if the target enzyme was not present (lane 5) or a non-target enzyme was present (lane 7), but that the target enzyme instead cleaved the loop transducer (lane 6) with some of the product as observed in lane 3 while the larger fraction formed a slower moving complex resulting from the cleaved loop transducer opening and hybridizing with the hairpin (intense band in lane 5). This was all as desired.

Figure 3B:
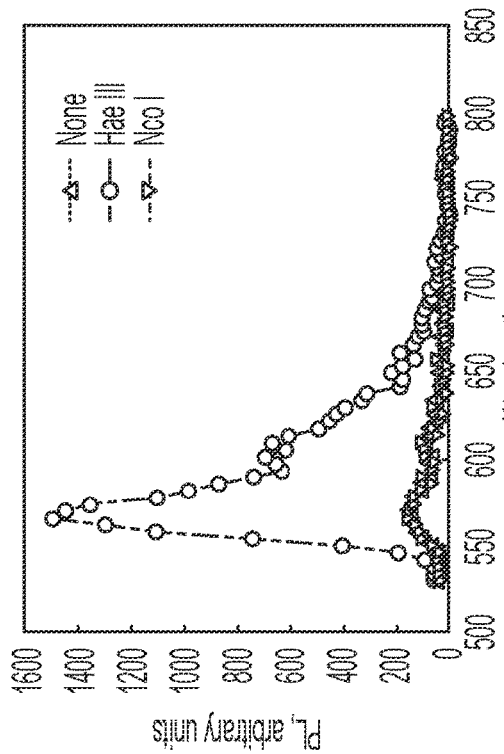
Figure 3C:
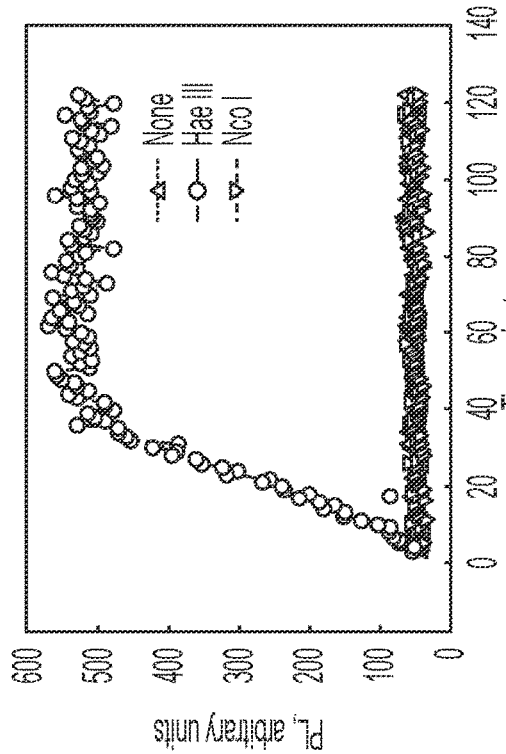
FIG. 3C shows the behavior of the system over time.
Figure 3A:
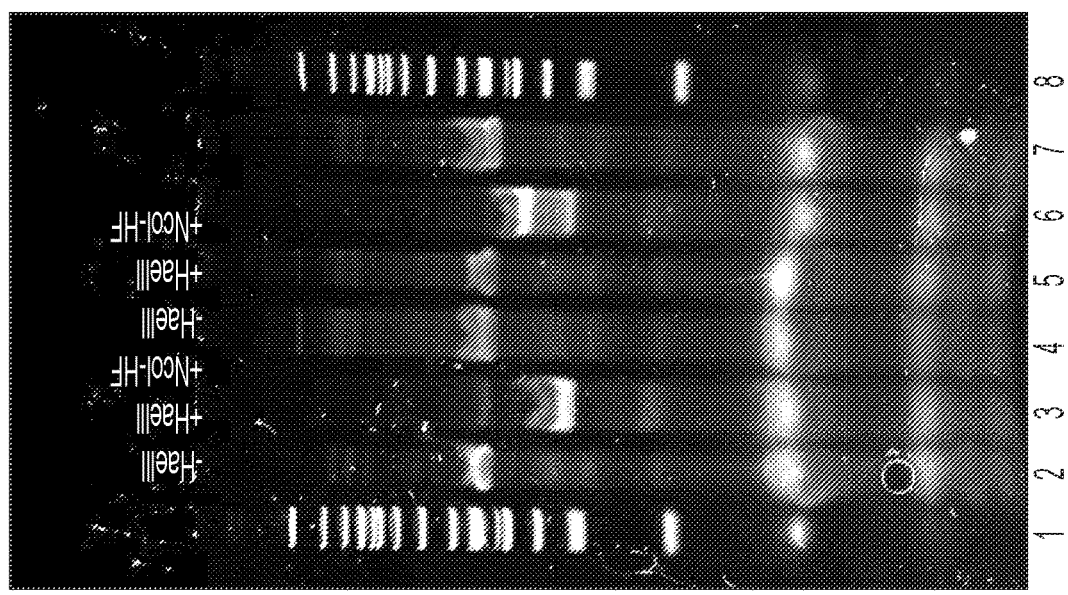
FIG. 3A is a gel demonstrating the desired behavior of the HaeIII loop sensor.

The molecular beacon was used as the output gate to follow the action spectroscopically with the data presented in FIG. 3B. This assay was also attractive in allowing tracking of the temporal evolution (FIG. 3C). With both the loop transducer and the output gate present, no change was seen in fluorescence if either the target enzyme was not present (upright triangles) or a non-target enzyme (NcoI-HF) was present (inverted triangles); this is as expected since under these conditions the loop transducer would not be cleaved and thus could not activate the molecular beacon. By contrast, in the presence of the target enzyme, the loop transducer would be cleaved, the beacon would be activated, and a sharp increase in fluorescence emission was indeed seen (green curves) with the reaction completing in about 40 minutes. This is near-ideal transducer behavior.

As a test of the modularity of the design, a loop transducer identical to that tested in FIGS. 3A-3C was prepared except that the recognition sequence was replaced with the target of NcoI-HF (CCATGG). Assessing its performance using a gel and fluorescence as above, it was found to function quite well, responding strongly to the presence of the target enzyme but not at all to a non-target enzyme (HaeIII). This demonstrates the modularity of the design and suggests that the approach could have broad applicability Protease Sensing Proteases are enzymes that cleave peptides, and therefore to create a loop sensor for proteases a peptide segment is preferably be used as the cleavage domain. For example, the protease trypsin targets an eight-residue peptide which was incorporated into the DNA loop. Before conducting physical experiments, a molecular dynamics simulation was performed in order to look for any undesired behavior, and especially for any unwanted interactions between the peptide and the DNA. The simulation confirmed (over its 200 ns duration) that the uncleaved loop transducer stayed in a stressed 'bow' configuration as depicted in FIG. 1, though of course there were thermal fluctuations. Moreover, the peptide showed no significant interaction with the DNA, and the peptide existed in a stretched-out conformation that should be available for attack by the protease.

The system behavior in the real world was examined using both a gel and fluorescence with the results shown in FIGS. 4A (lanes 1-3) and 4B. The data shows that the transducer does indeed operate as desired with the hairpin opened only when trypsin is present (lane 2) and not when it is either not present (lane 1) or when a non-target protease, namely the tobacco etch virus TEV protease, is present (lane 3). In addition, the transient spectroscopy in FIG. 4B shows more quantitatively that near-ideal sensor response is realized, with little leakage when no trypsin is present and with the full response to trypsin occurring in about 25 minutes. This modularity of the basic sensor system design was enabled by the non-specific mechanism of the loop stresses and topology that suppress leakage.

Figure 6:
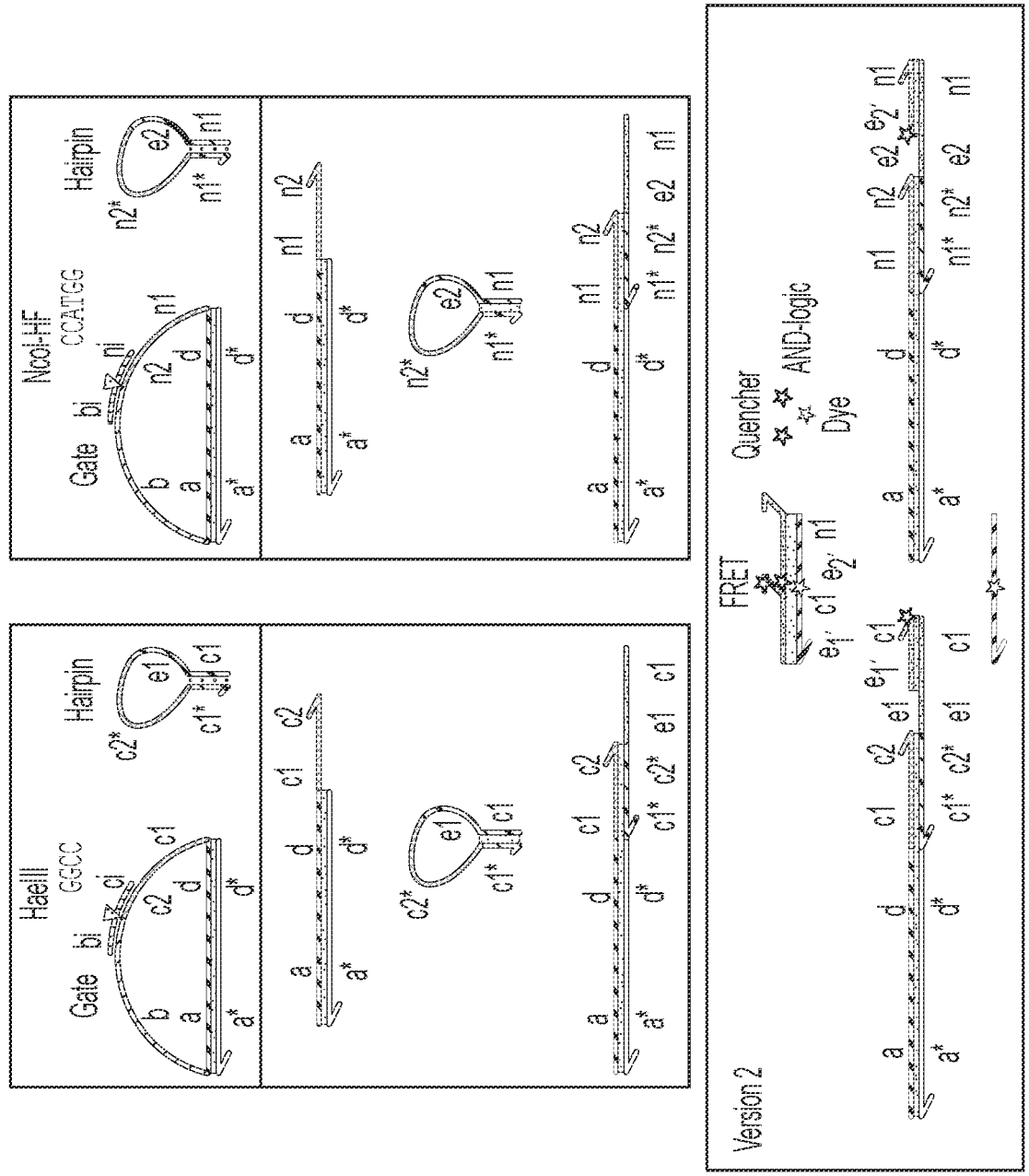
FIG. 6 shows DNA logic capable of implementing either OR or AND with a photoluminescent output.

As a second example of a protease transducer, a loop transducer was produced that was identical to that described immediately above except for having a cleavage domain for TEV protease (with target sequence of seven peptides) rather than for trypsin. The data for this transducer is shown in FIGS. 4A (lanes 4-6) and 4C. The gel showed the desired behavior when no protease was present (lane 4) and after TEV protease was added (lane 6). However, when a non-target protease (trypsin) was added, two intense bands were seen (lane 5) indicating that there is significant interaction of the loop transducer and the output gate. This is also seen in the transient fluorescence (FIG. 6C), though there is clearly a much stronger response to TEV protease. It is possible that this non-specific behavior of the TEV protease originates not in the loop transducer but in the protease's star activity at the non-optimal temperature of the experiment.

Logic

As shown herein, one can change target specificity of a system by modifying the cleavage domain to convert the activity of various enzymes into signals. An important benefit of performing this conversion is that the products of such sensors are readily combined to perform logical operations. This makes possible information processing of multiple data streams, to improve the reliability of the sensor output. Among other things, such designs can in principle greatly reduce false positive rates, e.g., by introducing an AND function that requires the presence of two different nucleases in order to giving a positive response.

Figure 5A:
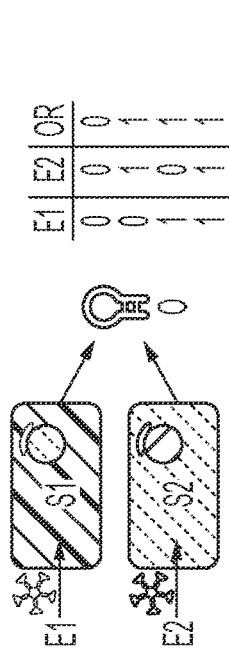
FIGS. 5A-5D illustrate the operation of OR/NAND logical gates.
Figure 5B:
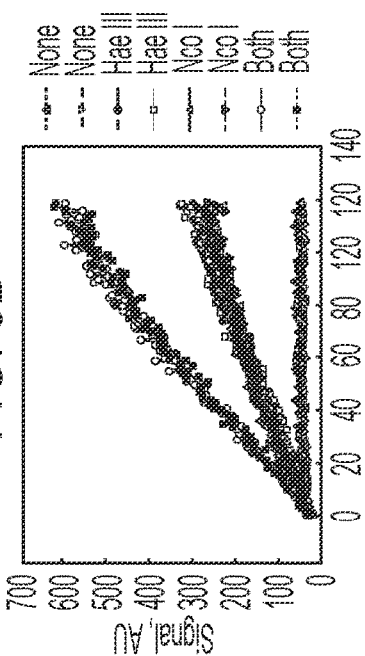
Figure 5C:
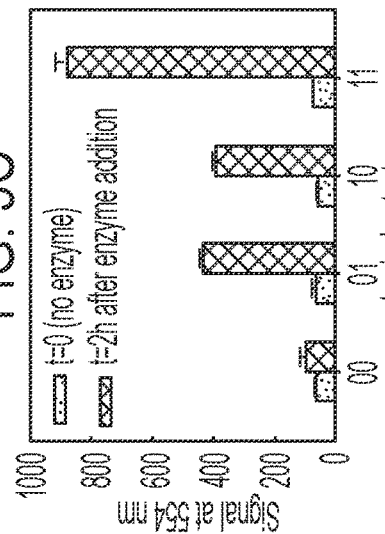
Figure 5D:
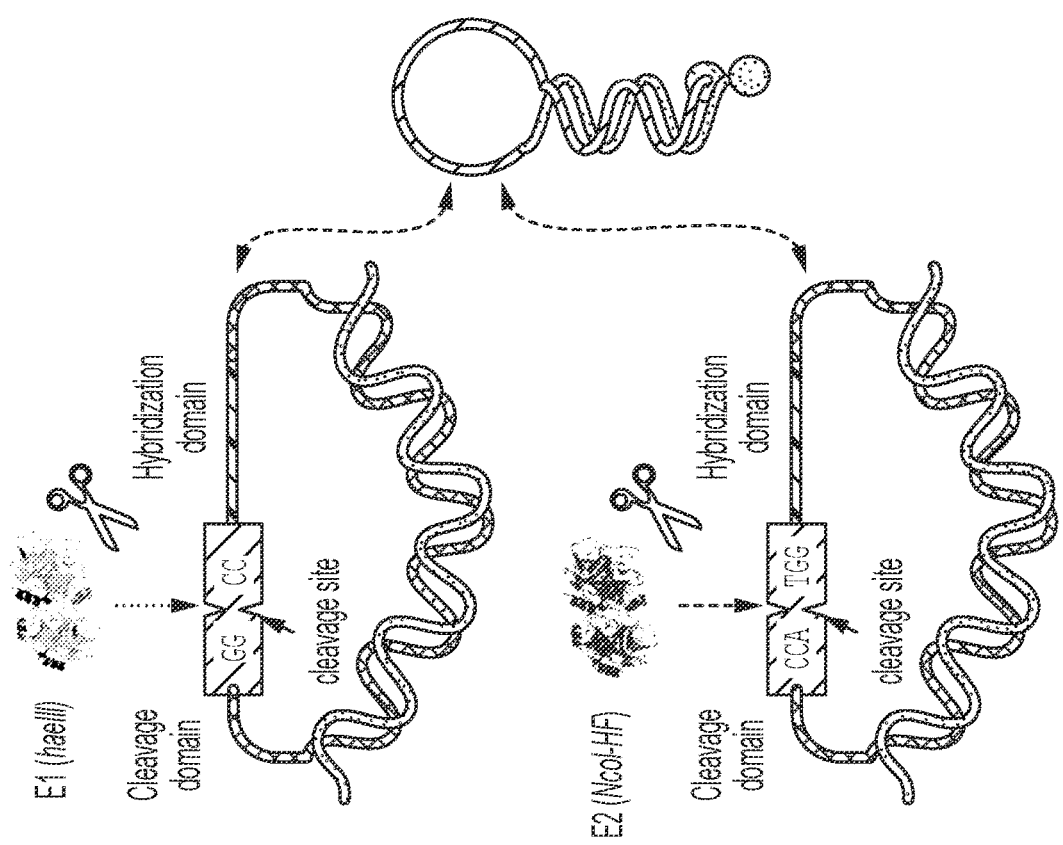
Figure 7:
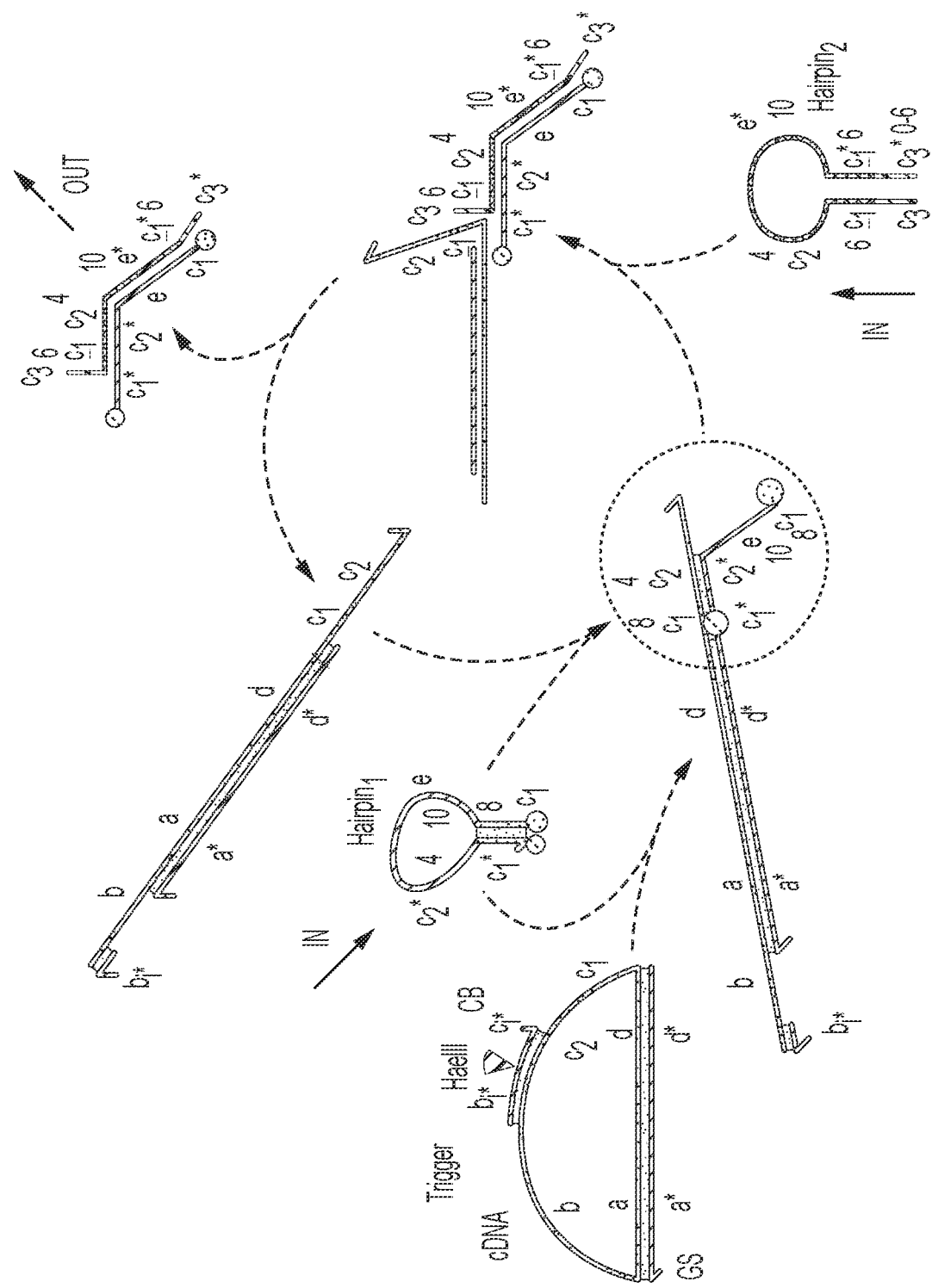
FIG. 7 illustrates a DNA amplification scheme.

One can create a Boolean OR gate or a NAND gate, specifically by creating two (or more) loop transducers with cleavage domains appropriate to two (or more) target enzymes but sharing the same sequence in their hybridizing domains that matches a particular molecular beacon. This idea is illustrated in FIGS. 5A and 5B for a 2-input OR-gate that detects either or both HaeIII and NcoI-HF. Upon sensing either or both enzymes, the corresponding loop transducer(s) hybridized to the molecular beacon, resulting in an increase in fluorescence as seen in FIG. 5C. In this design, the output gate (labeled hairpin) was functionalized with a donor-acceptor dye pair (Cye and Cy5), and opening of the hairpin resulted in a rise in the donor (Cy3) emission. A NAND functionality is achieved simply by monitoring the Cy5 dye instead. FIG. 5D gives the emission of the Cy3 dye before and 2 hours after the addition of either or both enzymes, and a clear increase in emission is evident when either or both enzymes are present in the solution. Interestingly, FIGS. 7C and 7D also show that the DNA "circuit"

acts not only as a binary OR gate, but as an analog adder as well. This same type of approach can be applied to a protease system.

One could feed the DNA output signals from multiple loop transducers into DNA logic circuits, and thereby achieve a modularity in which the transduction and logic functions are separated. As illustration, we here consider realizing an AND function on the outputs of two loop transducers using the design shown in FIG. 6. When both DNA outputs from the loop transducers are present, the labeled reporter duplex would self-assemble back into a stabilized hairpin and in that state provide a fluorescent output. Gel electrophoresis data showed sufficient results of the AND-gate construction.

Further generalizations are possible using methods like those in [4] and in other papers on DNA logic [8].

Amplification

Another use to which one can put the DNA output of the loop transducer is amplification. The process takes advantage of the catalytic capabilities of DNA oligonucleotides as exploited for example in [5]. A depiction of what should readily be possible is shown in FIG. 13.

Signal amplification is commonly used with sensors, typically by introducing gain into the electrical readout circuitry. For sensitive detection it is best to do this amplification as early as possible following transduction so as to minimize the amplification of noise. This suggests that for the loop transducers it would best to do the amplification at the molecular level rather than in subsequent optical or electrical stages. Two types of amplification at the molecular level can be considered, with one being inherent in the enzyme itself due to its turnover. The other is DNA amplification either using enzyme-dependent methods such as the polymerase chain reaction or rolling circle amplification (RCA), or with a DNA-based scheme that is enzyme-free.

The output DNA signals from the loop converter system can benefit from the integration of non-enzyme dependent amplification schemes. Due to the high amplification range of the catalytic hairpin assembly (CHA), the output DNA signals can be programmed as an input/catalyst to trigger the amplification process of CHA systems. A modified CHA amplification scheme for the proposed system was tested in the absence of the endonuclease-to-DNA signal converter. Fluorescence results indicate that the input signal was amplified at least 4× times using the modified CHA scheme. Since the modified CHA scheme only leveraged the internal-toehold mediate strand displacement in order to be compatible with the existing endonuclease-to-DNA signal converter, it was expected that the amplification factor was less optimal compared to those systems using the external-toehold mediated strand displacement. To improve the amplification factor, the hairpin structures of the modified CHA scheme were evaluated next. While maintaining the same structure of the first hairpin, the second hairpin's stem was padded with non-trivial bases to (i) increase its stability and (ii) minimize leaks in the absence of the catalyst strand. Fluorescence results indicate that the amplification factor linearly improved as a function of additional non-trivial bases. It is relevant that the proposed enzyme-to-DNA signal converter can be equipped with an amplification circuit to boost the output signal for low concentration detection applications.

Nucleic Acid Detection

Rather than as a detector of enzymes, the transducer can alternatively be used to detect ssDNA or RNA. The idea is that the oligo to be detected would hybridize to the cleavage domain of a nuclease transducer, thus making the latter susceptible to attack by an endonuclease and thereby revealing the presence of the target oligo. To illustrate, we considered an RNA biomarker as the target, with its binding to a loop transducer. In theory, any microRNA biomarkers could be targeted in this way. Gel electrophoresis and fluorescence spectroscopy confirmed the functionality of this design, with the RNA-DNA hybrid indeed being cleaved by the HaeIII endonuclease, thereby opening the loop and activating the molecular beacon. It is expected that a wide variety of nucleic acids could be detected in this way.

Further Embodiments

Beyond the above-demonstrated enzyme loop sensor effective for both endonucleases and proteases, it should be possible to develop similar schemes for other technologies such as microRNAs and engineered proteins such as zinc-finger nucleases.

The use of a peptide nucleic acid (PNA)-based approach should be possible either as the LS strand for increased rigidity and thermal stability, or as a facile and lower cost means of inserting a peptide into a DNA loop.

Beyond the demonstrated fluorescence outputs, color-change readouts should also be possible, e.g., with the DNA release driving a cross-linking reaction between particles (e.g., gold or magnesium). Or another embodiment could involve tethering to metallic surfaces so as to generate electrical outputs via standard electrochemical methods.

Also contemplated are designs with the hybridized LS and/or LC strands directly attached to the LL loop strand so that they would not get lost and hence could be reconstituted from a dried state.

The proposed system can be tethered to 2D substrates such as lipid bilayers via the cholesterol-labeled DNA oligomer for enhancing speed as well as utilizing the localization effect for sensing surface-bound biomarkers.

Signals from this system should be measurable by, circular dichroism (CD), UV-VIS, and excitonic-coupling phenomenon, in addition to the technqiues described in the examples.

Quenchers can be fluorescent dyes or other suitable quenchers of fluorescence as known in the art.

Advantages

Described herein is a new technique for enzyme detection/transduction by converting specific enzymatic activity into a DNA signal that can in turn be combined, processed, and/or amplified using known DNA methods. The advantages and new features of the method over existing approaches may be summarized as follows.

It provides a general technique that can be applied to endonucleases and proteases, and potentially also to many other classes of enzymes. This is made possible by the non-specificity of the principle of operation (based on the loop stiffness and topology) and by the demonstrated modularity of the design. These considerations should make the approach broadly applicable to many different areas in biomedicine, homeland security, etc.

The simplicity of the loop transducer design makes it scalable and makes possible the processing of other information beyond biomaterials.

With the loop transducer's simple DNA oligo output the technique can be readily coupled to the world of DNA nanotechnology, and especially to strand displacement networks. As illustrated in this disclosure, two primary functions achievable in this way are logical processing of the outputs and amplification of the outputs.

The nano-size, non-toxic nature, and robustness to enzymatic attack should make the approach adaptable to in vivo applications, unlike many alternatives.

The approach is accomplished at very low cost in view of the relative ease of obtaining the synthesized oligomers commercially. In standard storage conditions, shelf-life should be excellent given the known robustness of DNA.

The proposed system can withstand exonuclease digestion if using the circular loop for in vivo application.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

[1] N. Seeman, Structural DNA Nanotechnology (Cambridge Univ. Press, 2016).

[2] S. Tyagi and F. R. Kramer, "Molecular beacons: Probes that fluoresce upon hybridization," Nature Biotech. 14, 303 (1996).

[3] B. Yurke, "A DNA-fuelled molecular machine made of DNA," Nature 406, 605 (2000).

[4] G. Seelig, D. Soloveichik, D. Y. Zhang, and E. Winfree, "Enzyme-free nucleic acid logic circuits," Science 314, 1585 (2006).

[5] C. Wu et al., "A nonenzymatic hairpin DNA cascade reaction provides high signal gain of mRNA imaging inside live cells," J. Am. Chem. Soc. 137, 4900-4903 (2015).

[6] E. Protozanova, P. Yakovchuk, and M. D. Frank-Kamenetskii, "Stacked-unstacked equilibrium at the nick site of DNA," J. Mol. Biol. 342, 775 (2004).

What is claimed is:

1. An enzyme sensor system comprising:
   a loop transducer comprising a stiffening domain of about 30 to 55 base pairs in length, a cleavage domain cleavable by an enzyme of interest, and a first hybridizing domain of about 12 to 27 base pairs in length; and
   an output gate comprising a second hybridizing domain of about 8 to 15 base pairs in length and complementary to the first hybridizing domain, a fluorophore, and a quencher,
   wherein the system is configured so that in the absence of the first hybridizing domain, the quencher quenches the fluorophore, and upon hybridization of the two domains, the quencher become separated from the fluorophore sufficiently to allow fluorescence thereof.

2. The sensor system of claim 1, wherein the cleavage domain is cleavable by an endonuclease.

3. The sensor system of claim 1, further comprising a second output gate comprising a second fluorophore configured as a Forster resonance energy transfer partner of the first fluorophore.

* * * * *